United States Patent [19]
Roche et al.

[11] Patent Number: 5,512,577
[45] Date of Patent: Apr. 30, 1996

[54] BICYCLIC HEXAHYDROAPORPHINE AND 1-BENZYLOCTAHYDROISOQUINOLINE THERAPEUTIC COMPOSITIONS AND PROCESSES FOR UTILIZING SAID COMPOSITIONS

[75] Inventors: Victoria F. Roche, Bellevue; S. Edet Ohia, Omaha; Edward B. Roche, Bellevue, all of Nebr.

[73] Assignee: Creighton University, Omaha, Nebr.

[21] Appl. No.: 252,775

[22] Filed: Jun. 2, 1994

[51] Int. Cl.$^6$ .............................. A01N 43/42; A61K 31/44
[52] U.S. Cl. .................................................. 514/281; 546/43
[58] Field of Search .............................. 546/43; 514/281

[56] References Cited

PUBLICATIONS

Roche et al., Assessment of the in Vivo and in Vitro Opoid Activity of Bridged hexahydroaporphine and Isoquinoline Molecules, 1990, J. Med., Chem. pp. 245–248.

*Primary Examiner*—José G. Dees
*Assistant Examiner*—Rosalynd A. Williams
*Attorney, Agent, or Firm*—Benjamin Aaron Adler

[57] ABSTRACT

The invention relates to the method of synthesis of bicyclic hexahydroaporphine compounds which may provide improved therapy for diseases characterized by an increase in intraocular pressure. More specifically, the present invention relates to the preparation of agents which may provide for improved treatment of patients with glaucoma or ocular hypertension. The present invention describes the intraocular pressure lowering capabilities of several of the bicyclic hexahydroaporphine structures.

8 Claims, 7 Drawing Sheets

APOMORPHINE

N-METHYL-10-HYDROXY-
HEXAHYDROAPORPHINE

LEVORPHANOL

|   | $R_1$ | $R_2$ |   | $R_1$ | $R_2$ |
|---|-------|-------|---|-------|-------|
| 1 | $CH_3$ | CHO | 7 | $CH_3$ | H |
| 2 | $CH_3$ | $CH_3$ | 8 | $CH_3$ | CHO |
| 3 | H | $CH_3$ | 9 | $CH_3$ | $CH_3$ |
| 4 | $CH_3$ | H | 10 | H | $CH_3$ |
| 5 | $CH_3$ | $CH_2$—△ | | | |
| 6 | $CH_3$ | $CH_2CH=CH_2$ | | | |

BICYCLIC HEXAHYDROAPORPHINE AND 1-BENZYLOCTAHYDROISOQUINOLINE THERAPEUTIC COMPOSITIONS AND PROCESSES FOR UTILIZING SAID COMPOSITIONS

GOVERNMENT RIGHTS

The United States government has no rights in the invention.

CROSS REFERENCES

RELATED APPLICATIONS

The present application is an original patent application and is currently not known to be related to any co-owned and co-pending application.

TECHNICAL FIELD

The present invention is generally related to A-ring modified apormorphine analogs and more particularly to a process for producing hexahydroaporphines with a bicyclic A-ring which, along with their precursor bicyclic 1-p-substituted benzyloctahydroisoquinolines, may have significant therapeutic utility in the treatment of glaucoma and other forms of ocular hypertension.

BACKGROUND ART

For the past century, various chemical entities have been used to lower intraocular pressure in an attempt to prevent progressive vision loss in patients with glaucoma or other forms of ocular hypertension. Drugs that are currently employed in the therapy of glaucoma can be pharmacologically classified into the following groups: (a) direct and indirect parasympathomimetics (e.g. pilocarpine and echothiophate); (b) adrenergic agonists (e.g. epinephrine); (c) β and α-adrenergic antagonists (e.g. timolol and thymoxamine); (d) carbonic anhydrase inhibitors (e.g. acetazolamide); and, (e) hyperosmotic agents (e.g. glycerol). Although these drugs are effective in lowering intraocular pressure in a majority of glaucoma patients, they can cause distressing, and sometimes intolerable, side effects such as: (i) miosis, ciliary muscle spasm, retinal detachment and cataracts (by cholinergics); (ii) reactive hyperemia, burning and adrenochrome pigmentation (by adrenergic agonists); (iii) allergic reactions, burning and conjunctional hyperemia (by adrenergic antagonists); and, (iv) serum electrolyte imbalances and renal calculi (by carbonic anhydrase inhibitors). Furthermore, these drugs and hyperosmotic agents can cause significant systemic toxicity.

In the search for new and better antiglaucoma medications, several additional miscellaneous agents are currently being investigated. Among these are reduced benzoquinolines, isoproterenol, forskolin, cholera toxin, terbutaline, salbutamol, pirbuterol, vanadate, nylidrin, cannabinoids, prostaglandins, valinomycin, atriopeptins, neuropeptide Y, antazoline, ethacrynic acid, spironolactone, tetrahydrocortisol, angiotensin converting enzyme inhibitors, organic nitrates, melatonin, calcium channel blockers, tetracycline derivatives and haloperidol (M. B. Shields, *In Textbook of Glaucoma*, Third Edition, Williams & Wilkins, Baltimore, pp. 446–521, 1992). These compositions have been shown to be effective in lowering intraocular pressure in concentrations ranging from 0.001 to 10.0 percent.

The bicyclic hexahydroaporphines and 1-p-substituted benzyloctahydroisoquinolines described in this application are structurally distinct from any of the molecules currently available on the pharmaceuticals market or under clinical investigation. In addition, the highly lipophilic nature of these structures allows for effective penetration after topical administration in the eye. They represent a new class of potential antiglaucoma agents which may provide a safe and convenient route to the control of ocular hypertension.

The tetracyclic molecule known commonly as apomorphine (FIG. 2) is a well recognized non-selective agonist at dopamine receptors. The A-ring reduced analog (10-hydroxy-N-methyl-1,2,3,3a,11b, 11c-hexahydroaporphine, FIG. 2) has been generated by many as a byproduct of the Grewe synthesis of the tetracyclic morphinan opioid levorphanol (FIG. 2) but, to date, no therapeutic utility has been elucidated for hexahydroaporphinic molecules. The bicyclic N-formylhexahydroaporphine 1 (FIG. 3) was generated in theoretical yield during an attempt to produce a bicyclic analog of levorphanol through the reaction of the precursor bicyclic N-formyl-1-p-methoxybenzyloctahydroisoquinoline (8, FIG. 3) with anhydrous hydrofluoric acid. The additional bicyclic hexahydroaporphine and 1-p-substituted benzyloctahydroisoquinoline molecules shown in FIG. 3 were generated from the N-formyl analog, 8 through additional reductive or hydrolytic and substitution reactions.

DISCLOSURE OF INVENTION

The present invention describes the synthesis and use of bicyclic hexahydroaporphines and 1-p-substituted benzyloctahydroisoquinolines in the treatment of disease states characterized by elevated intraocular pressure. This invention relates to a method and compositions useful in controlling increases in intraocular pressure that precede the pathological changes associated with ocular hypertension and glaucoma. While the applicants are bound by no theory, it is postulated that these molecules, which contain the phenethylamine pharmacophoric unit common to the neurotransmitters norepinephrine and dopamine, may bind to presynaptic receptors which normally mediate the physiological actions of these endogenous transmitters. In so doing, release of transmitter from the presynaptic nerve terminals may be inhibited, thus resulting in a lowering of intraocular pressure due to either a diminished inflow or an enhanced outflow of aqueous humor. Furthermore, these molecules may act directly on postsynaptic receptors located in the iris/ciliary body complex to reduce aqueous humor production and/or on receptors located in the trabecular meshwork and uveoscleral channels to increase aqueous humor outflow.

If these mechanisms are subsequently proved, other therapeutic opportunities may present themselves. Specifically, since the bicyclic molecules depicted in FIG. 3 are lipophilic, they would be expected to exhibit central action after peripheral administration. Therefore, they could logically be expected to influence presynaptic neurotransmission in the brain, and could potentially find use in the treatment of hypertension (through the inhibition of norepinephrine release from central presynaptic terminals) or in neuroleptic disorders characterized by abberations in dopamine synthesis and release. Bicyclic 1benzyloctahydroisoquinoline structures 7 and 9 have shown highly selective $\beta_2$ agonist activity in isolated guinea pig trachea [Shams, G., Fedyna, J., Romstedt, K. J., Adejare, A., Miller, D. D., Roche, V. F., and Feller, D. R.; *Gen. Pharmacol.* 22(6), 1155(1991)]. Therefore, the bicyclic 1-benzyloctahydroisoquinoline and hexahydroaporphine molecules which share this pharmacologically relevant action could prove therapeutically useful as bronchodilating agents in the treatment of asthma, chronic obstructive pulmonary disease, and other respiratory disorders.

Thus, it is the primary objective of the present invention to provide methods of synthesis of chemical entities which will prove useful in the treatment of pathologic conditions characterized by increases in intraocular pressure, and which will retard or delay the progressive field of vision loss associated with ocular hypertension and glaucoma. In support of this objective, it has been demonstrated that intraocular pressure in the rabbit eye is significantly reduced compared to a control rabbit eye by topically administering as little as one drop of a 1% aqueous solution of the hexahydroaporphine compounds described in the present invention. A prolonged duration of pressure reduction was demonstrated with a single drop of a 1.5% solution of the secondary amine 4 (FIG. 7). It is anticipated that the bicyclic 1-p-substituted benzyloctahydroisoquinolines depicted in FIG. 3 could also provide this same desirable lowering of intraocular pressure, as their enhanced molecular flexibility will allow them to assume the conformation of the rigid bicyclic hexahydroaporphinic molecules in solution. In fact, their potency may actually be enhanced, as they may be able to adopt an even more favorable conformation which would result in higher affinity at target receptor surfaces. Pharmaceutical compositions containing bicyclic hexahydroaporphines and/or 1-p-substituted benzyloctahydroisoquinolines could be formulated as solutions, gels, ointments, suspensions or other suitable and well-tolerated ophthalmic delivery systems with an opthalmalogically acceptable vehicle thereof, selected from the group consisting of a preservative, and antioxidant and a buffer.

BRIEF DESCRIPTION OF THE DRAWING FIGURES

Figure 6:
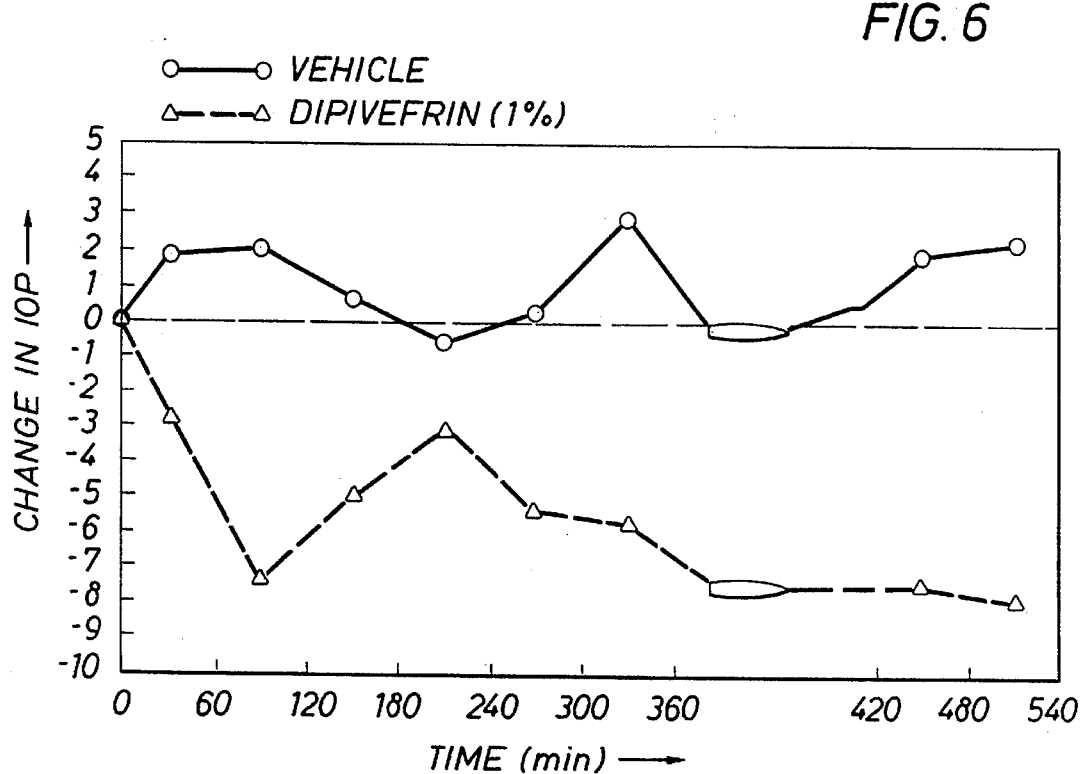

FIG. 6 shows a plot comparing rabbit eyes treated with either vehicle (water) or one drop of a 1% solution of the standard intraocular pressure lowering agent dipivefrin hydrochloride; and FIGS. 7–11 show plots comparing rabbit eyes treated with either vehicle (water) or one drop of a 1.0 or 1.5 percent aqueous solution of the bicyclic hexhydroaporphines 2–6 so that one may compare under similar conditions the intraocular pressure of eyes with and without treatment with the novel hexahydroaporphine structures.

MODES FOR CARRYING OUT THE INVENTION

A. Manufacture of bicyclic hexahydroaporphines and 1-p-substituted benzyloctahydroisoquinolines 1. Introduction The synthetic methods used to generate all compounds identified in FIG. 3, with the exception of compound 6, have been reported in the literature [Roche, V. F., Roche, E. B., and Nagel, D. L.; *J. Org. Chem.* 7, 1368(1982); Roche, V. F., Roche, E. B., Nagel, D. L., and McPhail, A. T.; *J. Org. Chem.*, 49, 3881(1984); Tran, N. D., Brosnahan, K. M., and Roche, V. F.; *J. Pharm. Sci.* 79(11), 1034(1990)].

Figure 4:
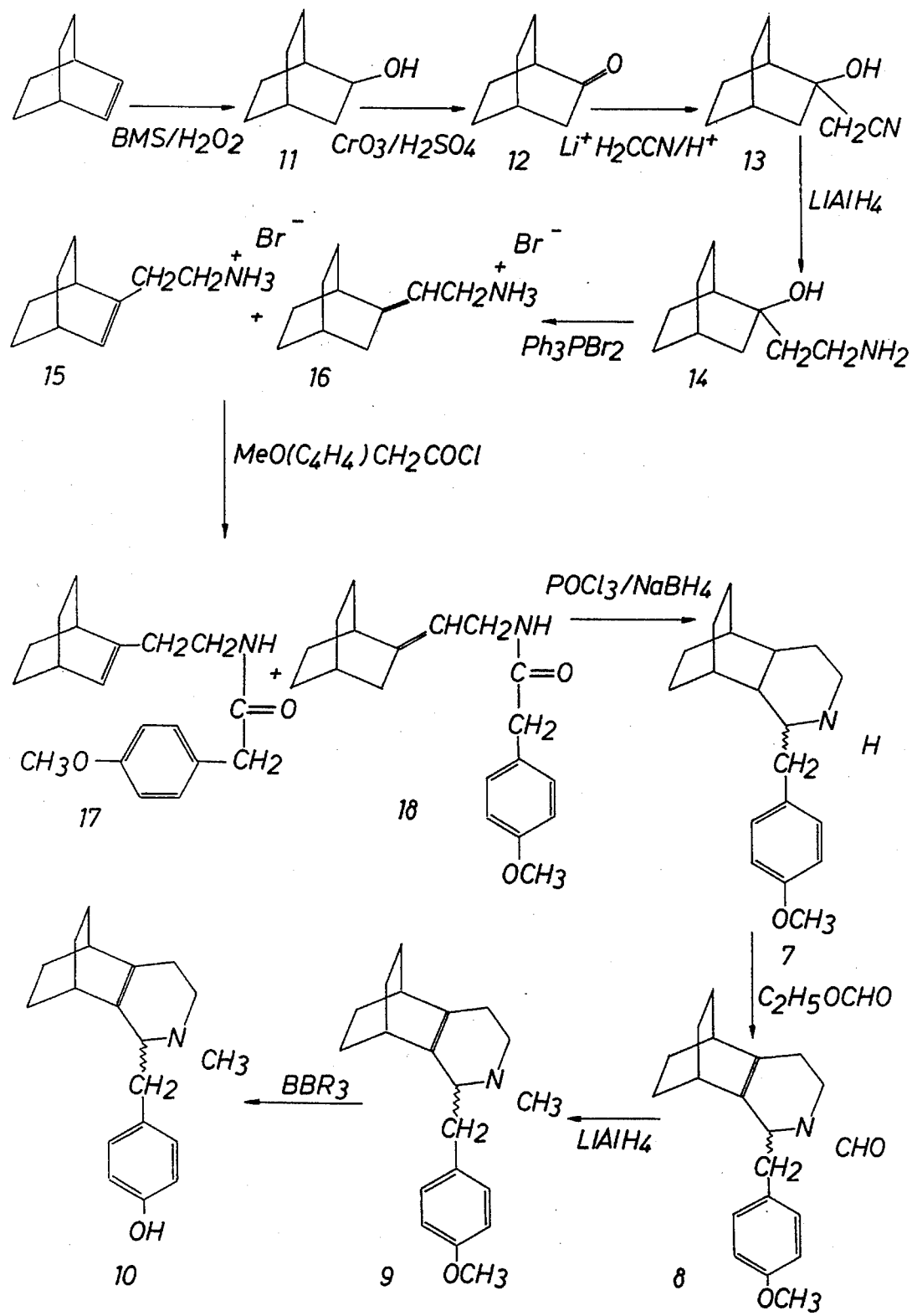
FIG. 4 is a diagrammatic illustration of the reaction pathway for the synthesis of bicyclic 1-p-substituted benzyloctahydroisoquinolines 7–10 of the present invention.
Figure 5:
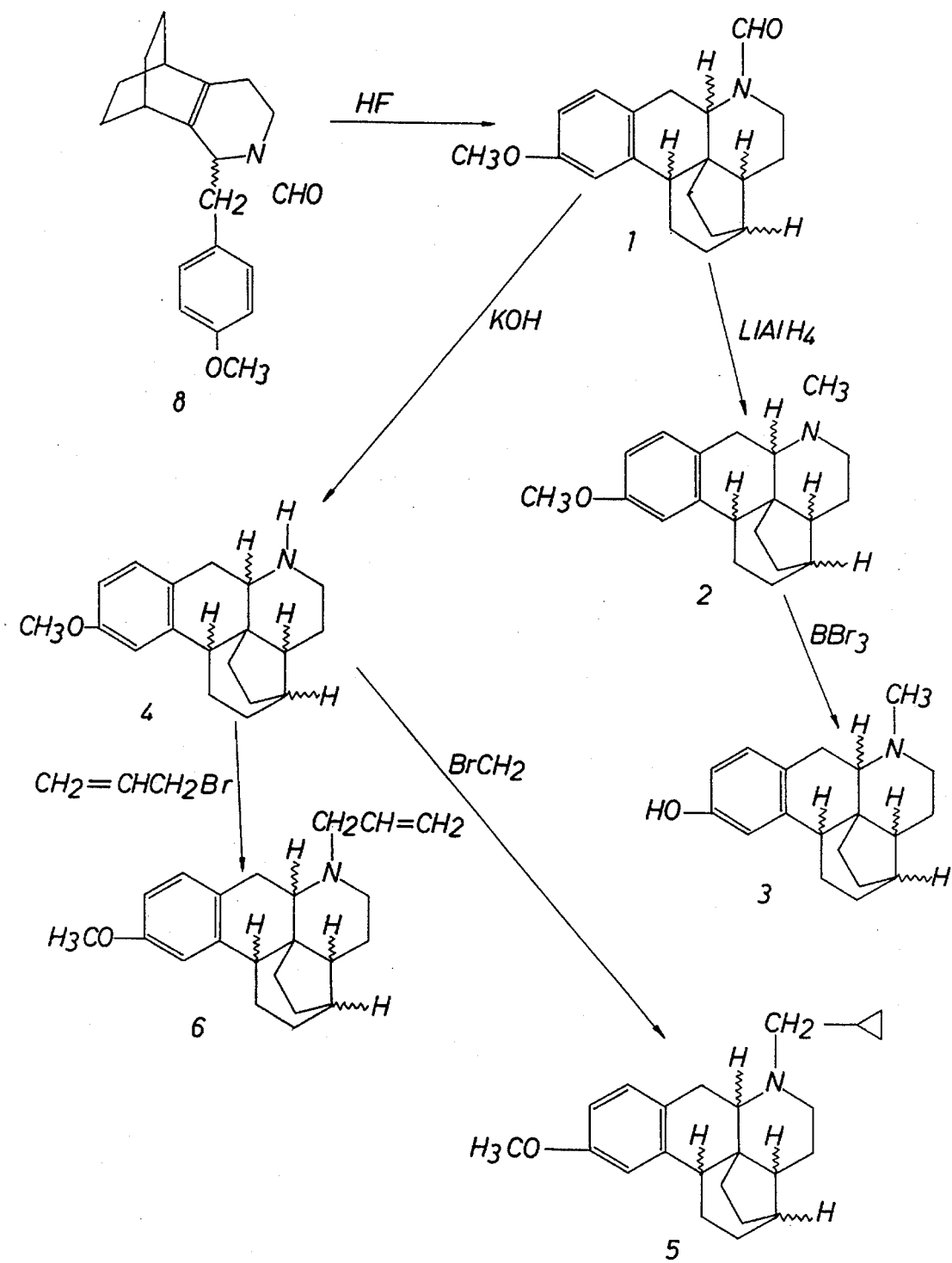
FIG. 5 is a diagrammatic illustration of the reaction pathway for the synthesis of bicyclic hexahydroaporphines 1–6 of the present invention.

It was the initial purpose of the syntheses outlined in FIGS. 4 and 5 to synthesize ±-5,8-endoethano-3-hydroxy-N-methylmorphinan. However cyclization of the racemic bicyclic N-formylisoquinoline precursor, 8, in liquified hydrofluoric acid proceeded with total rearrangement to give a nearly quantitative yield of ±-3,11c-ethano-6-formyl-10-methoxy-1,2,3,3a, 5,6,6a, 7,11b, 11 c-decahydro-4H-dibenzo[de,g]-quinoline (1), also known as 3, 11c-ethano-6-formyl-10-methoxy-1,2,3,3a, 11b11c-hexahydroaporphine. This cyclized structure was confirmed through X-ray crystallographic analysis of the reduced N-CH$_3$ analog in hydrochloride salt form. Hereafter, compounds in this class will be referred to simply as hexahydroaporphines, with the substituents at positions 6 (the amino nitrogen) and 10 identified.

2. Experimental

The proposed synthesis of 3 was based on a modification of the classic Grewe synthesis of morphinan which was modified by Schnider et al. for the production of levorphanol.

Scheme I outlines the synthetic procedure designed to produce 3 starting with bicyclo [2.2.2]oct-2-ene. Hydroboration of the bicyclic octene with borane-methyl sulfide (BMS) gave the bicyclic alcohol 11 in 70% yield. Chromic acid oxidation of 11, followed by cyanomethylation and lithium aluminum hydride reduction produced the amino alcohol, 14, in moderate yield. When free radical formation was inhibited, reaction of 14 with triphenylphosphine and bromine gave an equal mixture of two olefinic isomers 15 and 16. When free radical formation was not inhibited, a third product, which resulted from anti-Markovnikov addition of hydrogen bromide across the endocyclic double bond of 15, was also present in the crude reaction mixture. Acylation of the mixture of 15 and 16 with p-methoxyphenylacetyl chloride afforded the amides 17 and 18.

A Bischler-Napieralski cyclization reaction conducted with the mixture of amides 17 and 18 allowed isomer separation and, after sodium borohydride reduction, the desired secondary amine 7 was obtained in 42% yield from the isomeric primary amines. Intermediate 7 was formylated (8) and either cyclized in liquified hydrofluoric acid or reduced with lithium aluminum hydride to give 6-formyl-10-methoxyhexahydroaporphine 1 or the 2-methyl-1-p-methoxybenzyloctahydroisoquinoline derivative 9, respectively. The formylated hexahydroaporphine 1 was reduced with lithium aluminum hydride and O-dealkylated with boron tribromide to give the final product, 3 which was characterized as the hydrochloride salt. The p-methoxybenzyloctahydroisoquinoline derivative 9 was also O-dealkylated with boron tribromide and gave the 1-p-hydroxybenzyl derivative, 10.

In order to introduce the allyl and cyclopropylmethyl nitrogen substituents in the bicyclic hexahydroaporphine molecular series, the unsubstituted secondary amine 4 was first generated through the base-catalyzed hydrolysis of the N-formyl precursor 1. The nor derivative was then alkylated utilizing either cyclopropylmethyl bromide (to produce 5) or allyl bromide (to produce 6), The assigned structures of key intermediates were corroborated with $^{13}$C- and $^{1}$H NMR spectroscopy. X-ray crystallographic analyses have verified the structures of 2 and 8.

3. Synthetic Data.

Melting points were determined on either a MeI-Temp or a Fisher-Johns melting point apparatus and are uncorrected. Infrared spectra were recorded on either a Beckman IR-18A or a Perkin-Elmer 467 grating infrared spectrophotometer and are referenced to polystyrene. Proton NMR spectra were obtained with either a Varian EM-360 60 MHz or a Varian XL-300 300 MHz spectrometer and are referenced to tetramethylsilane or hexamethyldisiloxane. Carbon NMR spectra were obtained on a Varian LX-300 75MHz spectrometer and are referenced to tetramethylsilane. Mass spectra were recorded on an AEI MS9 mass spectrometer equipped with a MSS series 2000 electronics and control console and a VG series 2000 data system. Elemental analyses were conducted by Galbraith Laboratories, Inc., Knoxville, Tenn. Experimental values for percent carbon, hydrogen, nitrogen, oxygen (by difference) and chlorine (when appropriate) were all within ±0.4% of calculated values.

Bicyclo[2.2.2]octan-2-ol (11). Hydroboration of commercially available bicyclo[2.2.2]oct-2-ene was accomplished by reacting 1 equivalent of the octene with 0.37 equivalent of borane-methyl sulfide complex and 1.1 equivalent of hydrogen peroxide in anhydrous ethyl ether. The pure alcohol, as white crystals, was recovered in 70% yield after vacuum sublimation. mp 215° C.

Bicyclo[2.2.2]octan-2-one (12). To a solution of 11 in acetone was slowly added chromic acid oxidizing reagent until an orange color persisted. After neutralization with sodium bicarbonate and removal of acetone in vacuo the ketone was extracted into ethyl ether, dried over $MgSO_4$ and sublimed under vacuum. A 65–70% yield of 12 as colorless crystals was obtained. mp 174°–180° C.

2-(Cyanomethyl)bicyclo[2.2.2]octan-2-ol (13). Cyanomethylation of 12 was accomplished by adding 1.0 equivalent of 12 to 1.0 equivalent of acetonitrile and 1.1 equivalent of n-butyllithium in freshly distilled dry tetrahydrofuran at -78° C. The product was isolated as a thick oil that was of sufficient purity for use in subsequent reactions. A 70% yield of 13 as white plates could be obtained by crystallizing from ethyl ether/petroleum ether. mp 41°–42° C. $^1$H-NMR ($CDCl_3$) δ2.63 (s, 2H), 2.35 (s, 1 H), 1.63 (m, 12 H); IR ($CHCl_3$) 3560, 3450, 2240 $cm^{-1}$.

2-(2-Aminoethyl)bicyclo[2.2.2]octan-2-ol (14). A solution of 13 in anhydrous ethyl ether was added to a 2.4 molar excess of lithium aluminum hydride and stirred at room temperature for 4 h. After precipitating the metal hydroxides by the addition of water and 5N sodium hydroxide, 14 was isolated as white crystals in 70% yield. Further purification was accomplished by recrystallizing from ethyl ether/petroleum ether. mp 100°–101° C. $^1$H-NMR ($CDCl_3$) δ3.03 (t, 2 H), 2.78 (s, 3 H), 1.41 (m, 14 H); IR ($CHCl_3$) 3380, 3240, 1570, 1450, 1165, 1075 $cm^{-1}$.

2-(2-Aminoethyl)bicyclo[2.2.2]oct-2-ene hydrobromide (15) and 2-(2Aminoethylidene)bicyclo 2.2.2]octane hydrobromide (16). A 250 ml three-necked flask was heated at 210° C. for 8–12 h. Under a stream of dry nitrogen, the flask was charged with 100 ml freshly distilled p-xylene and 550 mg (2.1 mmole) of 99% triphenylphosphine. With vigorous stirring, 0.1 ml (1.9 mmole) bromine was added, and a precipitate formed. The mixture was heated to 80° C. to drive off unreacted bromine, and cooled to 40° C., at which time 328 mg (1.9 mmole) of 14 was added as a solid. Heating was reinitiated and, at 70°–80° C., a catalytic quantity of hydroquinone was added. The flask was covered to omit light and the solution heated to reflux. Thirty minutes after the evolution of hydrogen bromide could no longer be detected, the reaction was cooled and the product filtered. The xylene was washed three times with water, the filtered product added to the aqueous washings, and the aqueous solution lyophilized. A 77.8% yield of crude product, containing approximately equal amounts of 15 and 16 was obtained. The isomers could be separated by repeated recrystallization from a methanol/ethyl ether solution. Pure 15 decomposed at 229°–232° C. Pure 16 decomposed at 222°–225° C. 15 $^1$H-NMR ($D_2O$) δ 6.1 (2d, 1 H), 3.1 (t, 2 H), 2.43 (m, 4 H), 1.25 (m, 8 H). 16 $^1$H-NMR ($D_2O$) δ 5.22 (m, 1 H), 3.56 (d, 2 H), 2.27 (m, 3 H), 1.56 (m, 9 H).

p-Methoxyphenylacetyl Chloride. In a 500 ml three-necked flask, equipped with a power stirrer, condenser, and addition funnel was placed 6.036 g (0.036 mole) of 99% p-methoxyphenylacetic acid. To the acid, 2.64 ml (0.036 mole) of thionyl chloride (previously triple distilled over triphenyl phosphite) was added and the mixture was stirred 3 h at room temperature. The reaction was heated to 35°–40° C. for 25 h, benzene was added, and the excess thionyl chloride was removed by distillation. Distillation of the product under vacuum (79°–80° C. (0.125 mmHg)) afforded the chloride in 85–90% yield as a colorless to very pale yellow liquid with a characteristic odor: $^1$H NMR ($CDCl_3$) δ 5 7.07 (AA'BB',4 H, aromatic), 4.08 (s, 2 H, $CH_2$), 3.83 (s, 3 H, $OCH_3$); IR (neat) 1800 (C=O stretch), 1260 (C—O—C stretch, asymmetric), 1030 (C—O—C stretch, symmetric), 1510 (aromatic C=C stretch) $cm^1$.

[[[(p-Methoxybenzyl)carbon yl]amino]ethyl]bicyclo-[2.2.2[oct-2-ene (17) and 2-[[[(p-Methoxybenzyl)carbonyl] amino]ethylidene]bicyclo[2.2.2[octane (18). To a 250-ml single-necked flask, equipped with a magnetic stirrer, was added 4.27 g (0.018 mole) of an approximately equal mixture of the olefinic amine hydrobromides 15 and 16 in 150 ml of dry benzene. After the addition of 4.4 ml of dry pyridine, the mixture was stirred for 15 min, a solution of 3.89 g (0.018 mole) of p-methoxyphenylacetyl chloride in 25 ml of dry benzene was added, and the reaction was stirred for 4 h at room temperature. The precipitated pyridine salts were filtered and washed with benzene, and the combined organic phases were washed consecutively with 50 ml of dilute hydrochloric acid, 50 ml of water, 50 ml of dilute ammonium hydroxide, and three 50-ml portions of water. After drying ($MgSO_4$) and concentrating, a quantitative yield of a pale yellow oil was isolated. The $^1$H NMR spectrum of this oil indicated the presence of both the endocyclic (17) and the exocyclic (18) olefinic amides in approximately a 1:1 ratio based on the integration ratio of the isomeric olefinic protons. The oil was used in the next reaction without further purification: $^1$H NMR ($CDCl_3$)δ6 5.65 (d,1 H, 3-H), 5.00 (m, 1 H, 2-CH); IR (neat) 3300 (NH stretch), 1660 (C=O stretch), 1260 (C—O—C stretch, asymmetric), 1050 (C—O—C stretch symmetric) $cm^1$.

A sample of pure 17 as a yellow oil was synthesized for spectroscopic purposes by the above procedure, utilizing 50 mg of purified $^1$H NMR ($CDCl_3$) δ7.03 (AA"BB", 4 H, aromatic), 5.73 (d, 1 H, 3-H), 5.43 (m, 1 H, NH), 3.82 (s, 3 H $OCH_3$), 350 (S, 2 H, OC-$CH_2$), 3.25 (5, 2 H, $CH_2$N), 1.87–2.64 (m, 4 H, 1-H, 2-$CH_2$, 4-H), 0.67–1.67 (m, 8 H, remaining protons).

5, 8-Ethano-1 -(p-methoxybenzyl)- 1, 2, 3,4, 5, 6, 7, 8-octahydroisoquinoline (7). A 250 ml single-necked flask, equipped with a reflux condenser and a magnetic stirrer was charged with 5.38 g (0.018 mole) of the mixture of amides 17 and 18 in 150 ml of dry benzene. In one lot, 2.74 ml (9.030 mole) of phosphorus oxychloride was added and the mixture heated to reflux for 2 h. The reaction mixture was reduced in vacuo to a thick red syrup which was shaken vigorously with 50 ml of water and twice the volume of ethyl ether. The ether phase was extracted several times with 25–50 ml portions of water. The water was evaporated in vacuo, leaving 5.36 g of a honey colored tacky oil, corresponding to 0.0169 mole of intermediate imine hydrochloride. The oil was dissolved in 60 ml of water and the pH was adjusted to 5.0 with dilute sodium hydroxide solution. After transferring to a 250 ml one-necked flask and adding 100 ml of 95% ethanol, the flask was cooled in an ice bath and 1.54 g (0.0406 mole) of sodium borohydride was added as a solid in very small increments and with vigorous stirring. The reaction mixture was refluxed 1 h, and after ethanol evaporation, the aqueous solution was extracted four times with ether. All organic phases were combined, dried ($Na_2SO_4$), and concentrated to give a dark yellow oil which was distilled under vacuum with an air-cooled condenser (160°–170° C. (0.2–0.1 mmHg)). A thick, pale yellow oil (7) distilled in 41.6% overall yield from the isomeric amides: $^1$H NMR ($CDCl_3$) δ 5 7.02 (AA'BB', 4 H, aromatic), 3.77 (s, 3 H, $OCH_3$), 3.30–3.96 (m, 1 H, 1-H), 2.34–3.20 (m, 5 H, NH, 3-H $_3$, 1$CH_2$), 190–230 (m, 4 H, 4-$H_2$, 5-H, 8-H), 0.90–1.83 (m, 8 H, remaining protons); IR (neat) 3300 (NH stretch), 1245 (C—O—C stretch, asymmetric), 1040 (C —O—C stretch, symmetric) $cm^1$, mass spectrum, m/z 283 ($M^+$), 162 ($M^+$-p-methoxybenzyl, base), 91 (tropylium ion).

The amine 7 could also be purified via the formation of the oxalate or the methanesulfonate salts. The oxalate was recrystallized from acetone and melted at 142.5°–143° C. The methanesulfonate was purified from methanol:benzene (1:1 ) with ethyl ether added to induce crystallization: mp 132°–132.5° C.

5, 8-Ethano-2-formyl- 1 -(p-methoxybenzyl)- 1, 2, 3, 4, 5, 6, 7, 8-octahydroisoquinoline (8). The ethyl formate used in this reaction was purified immediately before use by storing 20 ml of purchased reagent over 3.0 g of sodium carbonate for 1 h with occasional swirling, followed by distillation from 1.0 g of phosphorus pentoxide. A 100 ml three-necked flask was equipped with a stirring bar, gas inlet adapter, condenser with attached drying tube, and a thermometer adapter. After the system was flushed with dry nitrogen for 15 minutes 1.12 g (0.0040 mole) of 7 in 50 ml of dry benzene was introduced, 12 ml (0.148 mole) of ethyl formate was rapidly added, the nitrogen flow was discontinued, and the reaction was heated to 50° C. for 18–24 h. Reaction progress was monitored by thin-layer chromatography (TLC) on silica gel 60, precoated glass plates (E. Merck) (5×20 cm), which were developed in acetone/dichloromethane (70:30) $R_f$ (7) 0.20, $R_f$ (8) 0.80. After removal of solvent in vacuo, the product was dissolved in ethyl ether and washed consecutively with water, 10% hydrochloric acid, and twice again with water. After drying ($MgSO_4$) and concentrating the remaining clear oily formamide 8, in 84% crude yield, was crystallized as colorless plates from a minimum amount of ethyl ether in 66% overall yield: mp 105°–106° C.; $^1$H NMR ($CDCl_3$) δ 7.32 (s, 1 H, CHO), 6.57–7.03 (m, 4 H, aromatic), 4.20–4.63 (m, 1 H, 1-H), 3.73 (s, 3 H, $OCH_3$), 2.53–3.15(m, 4 H, 1-$CH_2$, 3-$H_2$), 1.92–.2.53 (m, 4 H,4-$H_2$5-H, 8-H), 100–1.92 (m, 8H, remaining protons); IR (KBr) 2860 (aldehyde stretch, asymmetric), 1045 (C—O—C stretch, symmetric) $cm^{-1}$, mass spectrum, m/z 311 (M+), 190 (M+-p-methoxybenzyl, base), 121 (p-methoxybenzyl$^+$).

5, 8-Ethano-1 -(p-methoxybenzyl)-2-methyl- 1, 2, 3, 4, 5, 6, 7, 8-octahydroisoquinoline (9). A three-necked 100 ml flask was dried by heating in a high temperature oven at 210° C. for 18 h and allowed to cool under a stream of dry nitrogen. When totally cooled, 102 mg (2.67 mmole) of lithium aluminum hydride in 20 ml of anhydrous tetrahydrofuran (freshly distilled from lithium aluminum hydride) was introduced. With ice cooling and magnetic stirring, a solution of 300 mg (0.96 mmole) of 8 in 20 ml of tetrahydrofuran was added dropwise to the hydride. The mixture was then refluxed for 4–6 h or until TLC analysis in acetone/dichloromethane (70:30) indicated a completed reaction (silica gel 60, glass plates (5×20 cm): $R_f$(9) 0.19. The cooling bath was replaced and the excess hydride was cautiously decomposed by the slow addition of 100 μl of water, 100 μl of 15% sodium hydroxide, and 300 μl of water. A granular precipitate resulted which was filtered and triturated three times with ethyl ether. The organic filtrate was removed in vacuo, the residue was dissolved in ether, and all organic phases were combined and dried ($Na_2SO_4$). Concentration left 301 mg of 9 as an off-white oil (100% crude yield).

The hydrochloride monohydrate salt of 9 was prepared in 79% crude yield from the base and recrystallized from acetone: mp (sealed tube) 178°–180° C; $^1$H NMR (base in $CDCl_3$) δ 6.97 (AA'BB', 4 H, aromatic), 3.78 (s, 3 H, $OCH_3$), 2.87–3.27 (m, 1 H, 1-H), 2.40–2.87 (m, 4 H, 1-$CH_2$, 3-$H_2$), 2.33 (s, 3 H, $NCH_3$), 1.83–2.27 (m, 4 H, 4-$H_2$, 5-H, 8-H), 1.03–1.77 (m, 8 H, remaining protons); IR (KBr) 3460 (OH stretch), 2600–2460 ($NH^+$ stretch), 1245 (C—O—C stretch asymmetric), 1035 (C—O—C stretch, symmetric) $cm^1$; mass spectrum, m/z 297 ($M^+$), 176 ($M^+$- p-methoxybenzyl, base), 148 (retro-Diels-Alder), 121 (p-methoxybenzyl $^+$), 42 ($CH_2$=N=$CH_2^+$).

5.8-Ethano-1-(p-hydroxybenzyl)-2-methyl- 1,2,3,4,5,6,7, 8-octahydroisoquinoline (10). A 100 mL three-necked flask was dried for 24 h at 210° C. While cooling under a stream of dry nitrogen, the flask was immersed in an ethanol/dry ice bath and cooled to −75° C. Boron tribromide (300 μl, 3.16 mmole) was introduced, followed by 10 ml of dry dichloromethane. Purified 9 (224 mg, 0.754 mmole), as the base, in 30 ml of dry dichloromethane was added in a dropwise fashion. Thirty minutes after the addition of 9, the stirring was stopped, the nitrogen was replaced by a calcium sulfate drying tube, and the mixture was left in the cold for 12 h. After refluxing for 1 h, the reaction mixture was recooled in an ice bath and 3.5 ml of 10% ammonium hydroxide was slowly added and a flocculent precipitate formed. After stirring for 15 min, the cold bath was removed and 50 ml of water was added. The subsequent isolation of the product was conducted in the dark to minimize photooxidation. The phases were separated, the dichloromethane was removed in vacuo and the residue was dissolved in ethyl ether. The aqueous phase (pH 8.4) was adjusted to pH 9.1 with 10% ammonium hydroxide and extracted eight times with 20 ml portions of ether. All ether phases were combined, dried ($Na_2SO_4$), and concentrated to give a yellow oil. An attempt was made to purify this base by methansulfonate salt formation, but this salt form resisted crystallization. The hydrochloride salt was made and recrystallized from acetone/ethanol/ethyl ether in 29% yield. There was evidence of additional product in the mother liquor but it resisted crystallization: mp (sealed tube) 218°–220° C. sublime; $^1$H NMR (base in $CDCl_3$) δ 6.67 (AA'BB', 4 H aromatic), 4.58 (s, 1 H, OH), 2.87–3.30 (m, 1 H, 1-H), 2.43–2.87 (m, 4 H, 1-$CH_2$, 3-$H_2$), 2.33 (s, 3 H, $NCH_3$), 1.90–2.27 (m, 4 H, 4-$H_2$, 5-H, 8-H), 0.93–1.72 (m, 8 H, remaining protons); IR (base, neat) 3300 (OH stretch) $cm^{-1}$; mass spectrum, m/z 283 ($M^+$), 176 ($M^+$-p-hydroxybenzyl, base), 148 (retro-Diels-Alder), 107 (p-hydroxybenzyl$^+$), 106 (p-hydroxybenzyl-1$^+$), 42 ($CH_2$=N=$CH_2^+$).

3,11c-Ethano-6-formyl-10-methoxy-1,2,3,3a, 11b, 11c-hexahydroaporphine(1). To 402 mg (1.29 mmole) of thoroughly dried formamide 8 in a nitrogen-flushed 125 ml teflon bottle was cautiously added 90–95 mL of liquified hydrogen fluoride. The bottle was quickly capped and the solution was stirred overnight. After 15 h, nitrogen was again swept through the system to aid in removing the gaseous hydrogen fluoride. The red oily product was dissolved in 50 ml of chloroform and shaken with an equal volume of 10% ammonium hydroxide. The aqueous phase was extracted four times with 25 ml portions of chloroform and all organic extracts were combined and dried ($MgSO_4$). Removal of the chloroform in vacuo left derivative 1 as a pale yellow oil in 90–100% crude yield: $^1$H NMR ($CDCl_3$) δ 8.13 (s,1 H, CHO), 6.57–7.20 (m, 3 H, aromatic), 4.53–4.90 (m, 1 H, 6a-H), 3.80 (s, 3H, $OCH_3$), 1.00–3.70 (m, 17H, remaining protons); TLC acetone/dichloromethane (70:30), silica gel 60 glass plates (5×20 cm) $R_f$ (8) 0.79, $R_f$ (1) 0.71. The product (1) was not characterized further in this form, but rather was directly converted to the N-methyl derivative (2) for structural verification.

3, 11c-Ethano-10-methoxy-6-methyl-1,2,3,3a, 11b, 11c-hexahydroaporphine (2). Utilizing 393 mg (1.26 mmole) of the formamide 1 and 144 mg (3.78 mmol) of lithium aluminum hydride, a reduction reaction identical to that described for the synthesis of the 2-methyl-p-methoxybenzyloctahydroisoquinoline derivative (9) was performed. After drying and concentrating, 2 was isolated in 94% crude yield as a thick yellow oil. The hydrochloride monohydrate salt was prepared and recrystallized from acetone in 50% yield from the crude base: mp (sealed tube) 138°–139° C. dec; TLC acetone/dichloromethane (70:30), silica gel 60 glass plates (5×20 cm) $R_f$ (2) 0.19; mass spectrum, m/z 297 ($M^+$), 282 ($M^+$- $CH_3$), 148 ($M^+$-$C_{10}H_{13}O$, base), 121 (p-methoxybenzyl$^+$), 91 (tropylium ion); IR (KBr) 3396 (OH stretch), 2506 ($NH^+$stretch), 1240 (C—O—C stretch, asymmetric), 1060 (C—O—C stretch, symmetric) cm$^{-1}$.

The free base was regenerated from the purified hydrochloride salt and was further characterized: mp (sealed tube) 72°–74° C; $^1$H NMR ($CDCl_3$) δ 6.55–7.20 (m, 3 H, aromatic) 3.75 (s, 3 H, $OCH_3$), 2.55–3.15 (m, 3 H, 6a-H, 5-$H_2$), 2.32 (s, 3 H, $NCH_3$), 1.00–2.55 (m, 15 H, remaining protons).

3,11c-Ethano-10-hydroxy-6-methyl-1,2,3,3a, 11b, 11c-hexahydroaporphine(3). Utilizing 389 mg (1.31 mmole) of the hexahydroaporphine 2 and 350 μl (3.69 mmole) of boron tribromide, a dealkylation reaction identical with the one described for the synthesis of the isoquinoline derivative (10) was conducted. After reflux the flask was cooled to 0°–5° C. at which time 20 ml of ice water was cautiously added, and the mixture was stirred for 30 min. In the dark, the phases were separated, and the extraction procedure continued as described for the synthesis of 10. After concentrating, a yellow oil was isolated which was immediately converted to the hydrochloride salt. The salt was recrystallized from methanol/ethyl ether and gave a 42% yield of a white crystalline solid: mp (sealed tube) 273°–275° C. dec; $^1$H NMR (base in $CDCl^3$) δ 6.27–6.93 (m, 3 H, aromatic), 6.03 (brs, 1 H, 2 OH), 2.63–3.17 (m, 3 H, 6a-H, 5-$H_2$), 2.30 (s, 3 H, $NCH_3$), 1.03–2.57 (m, 15 H, remaining protons).

3,11c-Ethano-10-methoxy-1,2,3,3a, 11b, 11c-hexahydroaporphine (4). To 108 mg (0.347 mmole) of 1 in 2 ml of 95% ethanol was added 2 ml of 5M potassium hydroxide. The solution was refluxed for 60 h and concentrated to a paste. The paste was taken up in water and extracted three times with ethyl ether. The ether was washed three times with 5% HCl, the aqueous phase basified with 10% NaOH, and extracted three times with ethyl ether. The ether was dried over $MgSO_4$, and the secondary amine 4 isolated as a straw colored oil in 74% yield. Conversion to the hydrochloride salt and recrystallization from methanol/ethyl ether provided a 67% yield of 4 hydrochloride as a white powder mp 230°–235° C. $^1$H-NMR ($d_4$-methanol) δ 7.16–6.77 (m, 3 H), 3.78 (s, 3H); IR (KBr) 2823, 2753 ($NH_2^+$ stretch), 1230 (C—O—C stretch, asymmetric), 1131 (C—O—C stretch, symmetric).

6-Cyclopropylmethyl-3,11c-ethano-10-methoxy-1,2,3, 3a, 11b, 11c-hexahydroaporphine (5). A 15 ml two-necked flask was dried overnight at 200° C. Under dry nitrogen, the flask was charged with 100 mg (0.313 mmole) of 4 hydrochloride, 57.8 (0.688 mmole ) of sodium bicarbonate, 2 ml dry dimethylformamide, and 50 μl (0.5053 mmole) of cyclopropylmethyl bromide. The solution was stirred and heated at 100° C. for 24 h. Following solvent removal in vacuo, extraction into ethyl ether or benzene, and drying over $MgSO_4$, 5 was isolated as a thick pale yellow oil. The hydrochloride salt was recrystallized from methanol/ethyl ether in 68.4% yield. mp 204°–212° C. $^1$H-NMR ($d_4$-methanol) methanol) δ 7.22–6.77 (m, 3 H), 4.21–4.15 (t, 1H), 3.79 (s, 3 H); IR (KBr) 2985 (C-H stretch), 2680–2660 ($NH^+$ stretch), 1600–1545 (C=C stretch), 1452 (cyclopropane C—C stretch), 1450–1425 (C—H out of plane bend), 1231 (C—)—C stretch, asymmetric), 1032 (C—O—C stretch, symmetric) cm$^{-1}$.

6-Allyl-3,11c-ethano-10-methoxy-1,2,3,3a, 11b, 11c-hexahydroaporphine (6). Utilizing allyl bromide in place of cyclopropylmethyl bromide, an alkylation identical to the one described for the synthesis of 5 was conducted. After work-up of the free base, the hydrochloride salt was generated and recrystallized from methanol/ethyl ether to give a beige precipitate in approximately 80% yield. Further recrystallization from acetone produced colorless plate-like crystals in approximately 75% yield. mp 135° C.

Crystal Data. 8: $C_{20}H_{25}NO_2$, $M_r$ 311.43, monoclinic, a −10.933 (4) Å, b =7.885 (3) Å, c =10.185 (4) Å, β=102.74 (1)°, U =853.1 Å$^3$, Z =2, $D_{calcd}$=1.212 g cm$^{-3}$. Absorption coefficient for Cu Ka radiation (Å1.5418 Å) $_u$=6.2 cm$^{-1}$. Space group $P_2(C_2^2)$ or $P2_1/m(C_{2h}^2)$ from systematic absences: 0k0 when k ≠2n; required to be the former since 8 lack either a center or mirror plane of symmetry.

2 hydrochloride: $C_{20}H_{28}(ClNO°H_2O)$, m, 351-93, a =37.622 (19) Å, b- 10.166 (5) Å, c =22.416 (11) Å, β=112.88 (1)°, U =7899 Å$^3$, Z =16,$D_{calcd}$=1.212 g cm$^{-3}$. Absorption coefficient for CUKa radiation, $_u$ =18 cm$^{-1}$. Space group $Cc(C_s^4)$ or $C2/c(C_{2h}^6)$ from systematic absences: hkl when h +k ≠2n, h0l when l ≠2n; shown to be the latter by structure solution and refinement.

B. Evaluation of bicyclic hexahydroaporphines as agents to decrease intraocular pressure 1. Experimental Male Albino rabbits (New Zealand strain) weighing 2–2.5 kg were purchased from Gary Smith, Inc. (Harlan, Iowa) and conditioned on 12 hour light-dark cycle. Animals were maintained and used in accordance with current National Institute of Health Guidelines and the Association for Research in Vision and Ophthamology (ARVO) Resolution in the use of animals in research. Intraocular pressure (IOP) measurements were conducted on restrained, awake animals using a calibrated Alcon pneumatonometer after topical application of proparacaine (0.5%). Baseline IOPs were measured in each animal two days before each test. Each group of rabbits received a dose of bicyclic hexahydroaporphine 2-6 and each dose was only tested once in each animal. After pretreatment with proparacaine, the right eye of each animal was treated with 50 μl of a bicyclic hexahydroaporphine (0.125–1.5%) and the other eye treated with 50 μl distilled water (vehicle). For each animal, baseline IOP was measured at 9:00 a.m. and then a 50 μl drop of drug (or vehicle) was applied to the eye. IOP measurements were made at 30, 60, 90 mins. and every 60 minutes thereafter for up to nine hours.

2. Results

Figure 7:
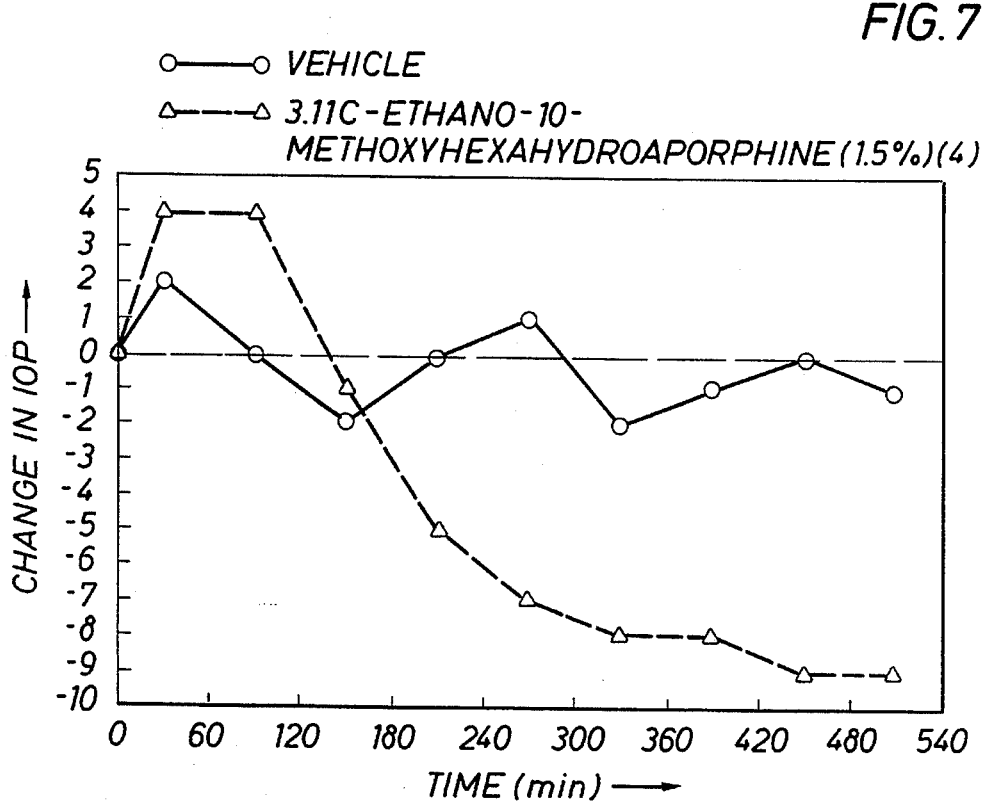
Figure 8:
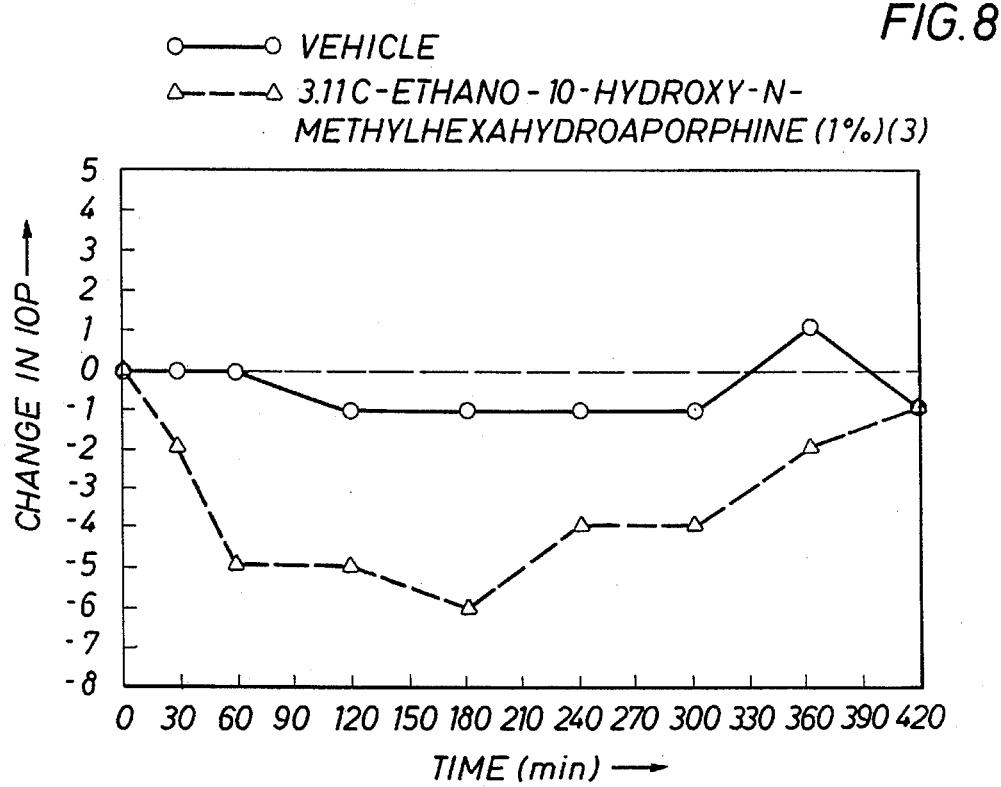
Figure 9:
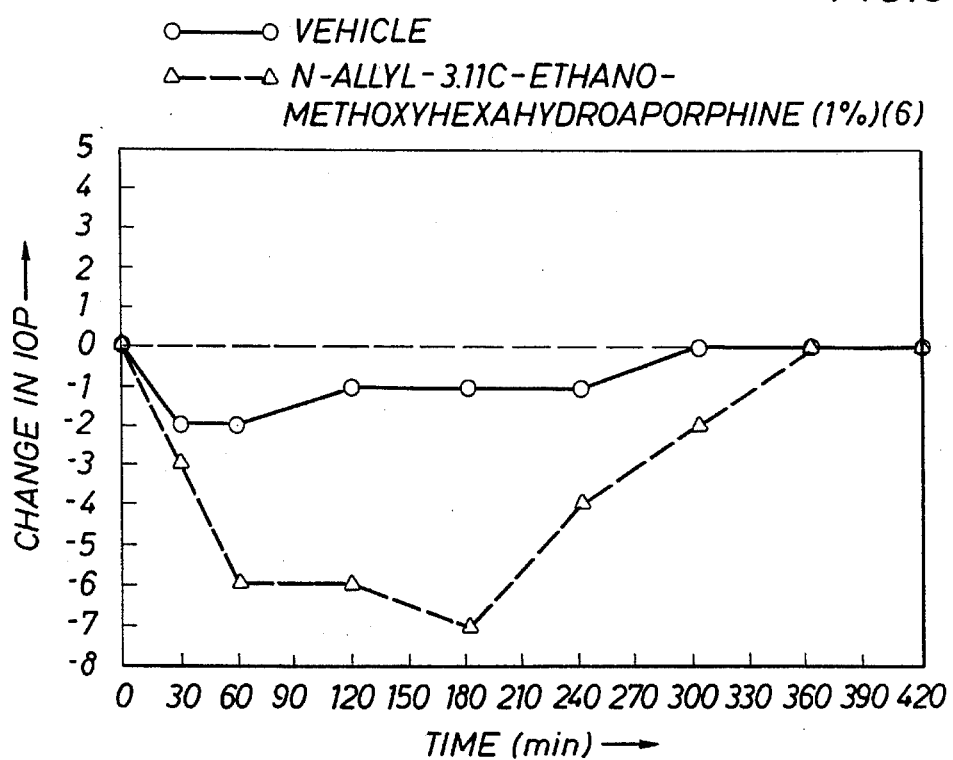
Figure 10:
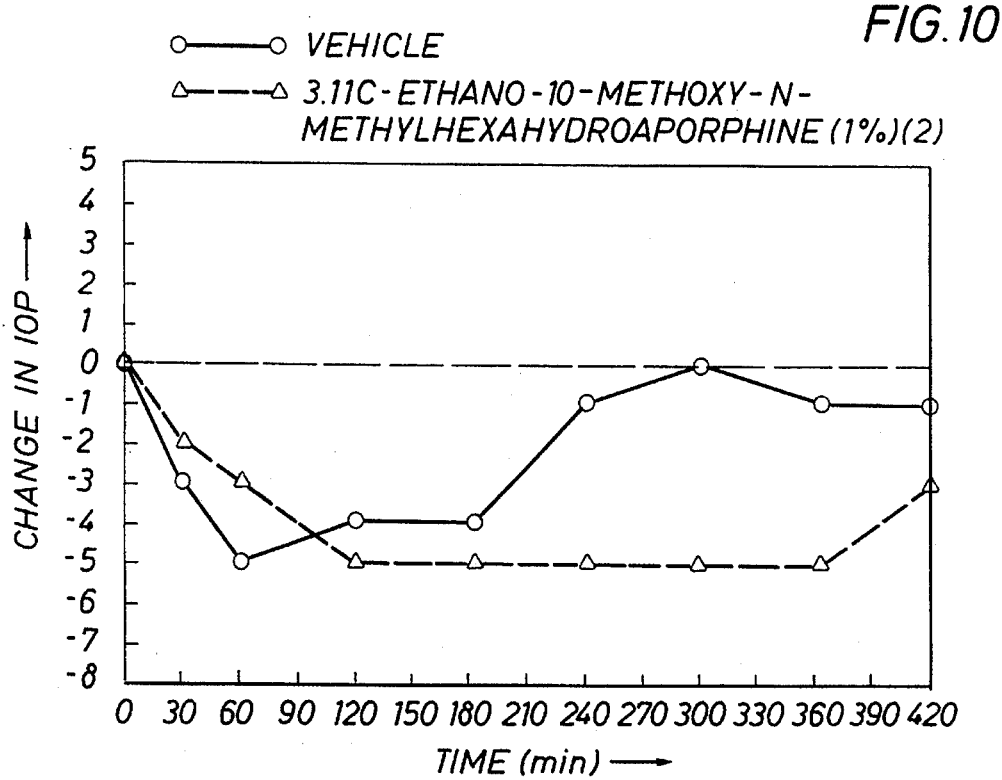
Figure 11:
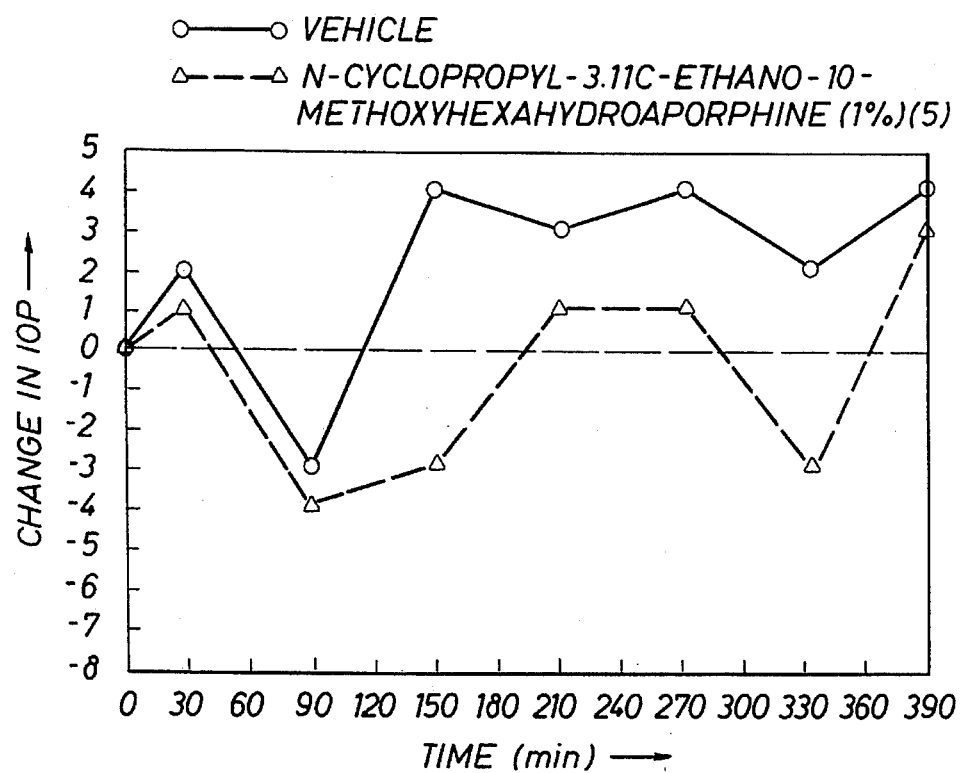
Figure 1:
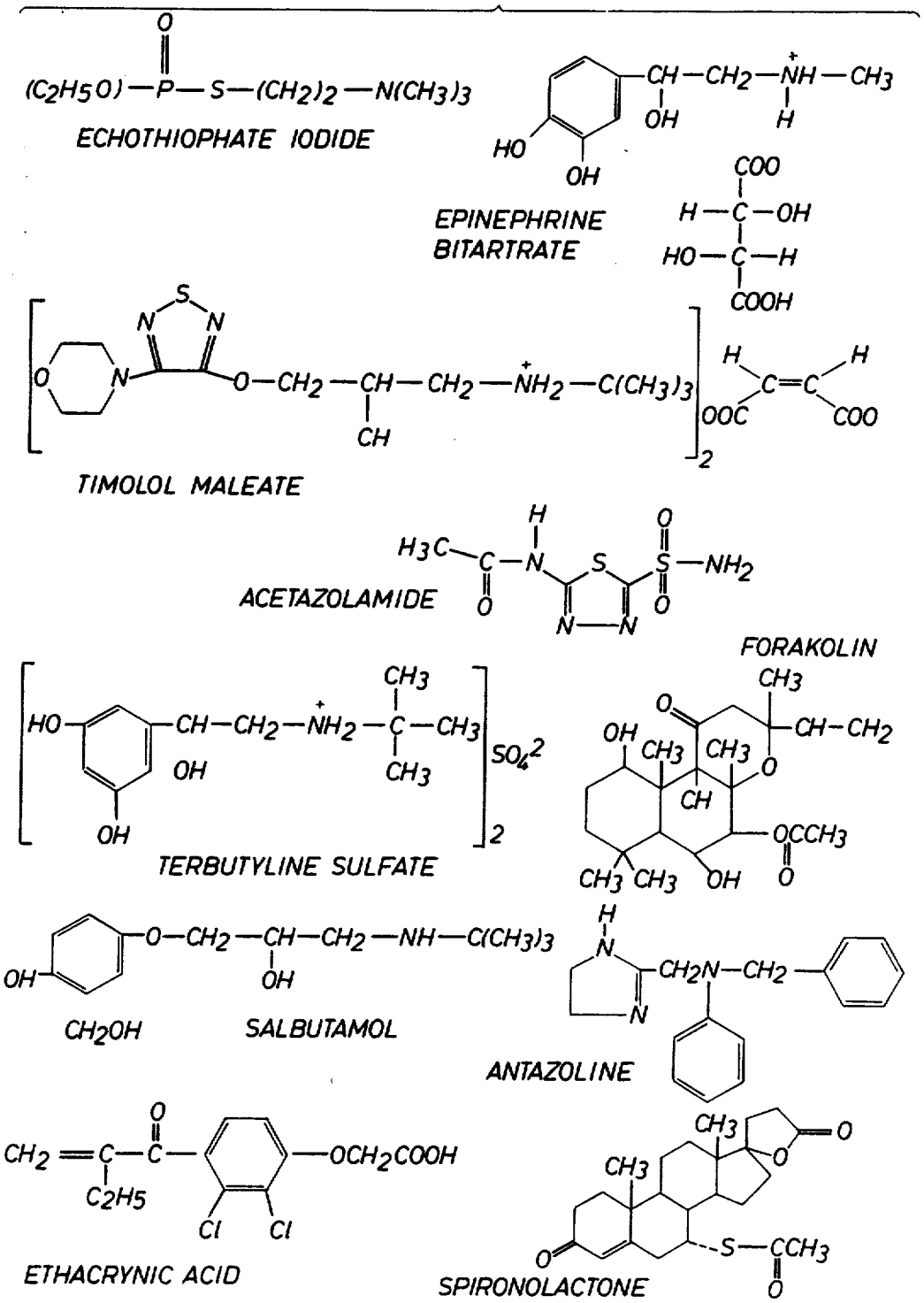
Figure 2:
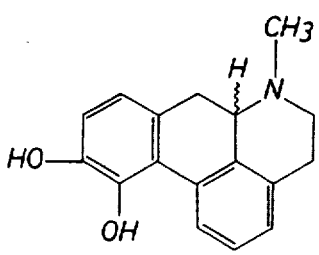
Figure 2:
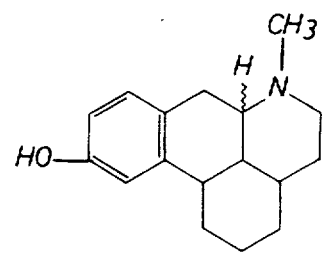
Figure 2:
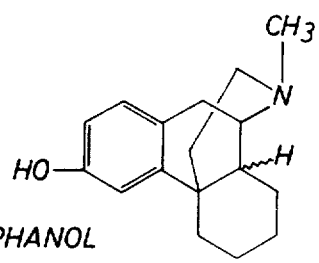
Figure 3:
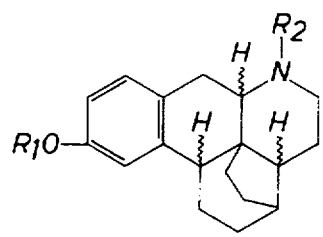
Figure 3:
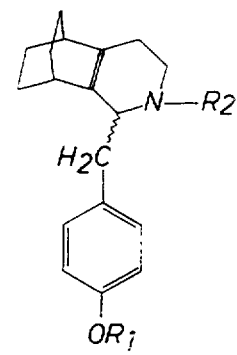
Figure 4:
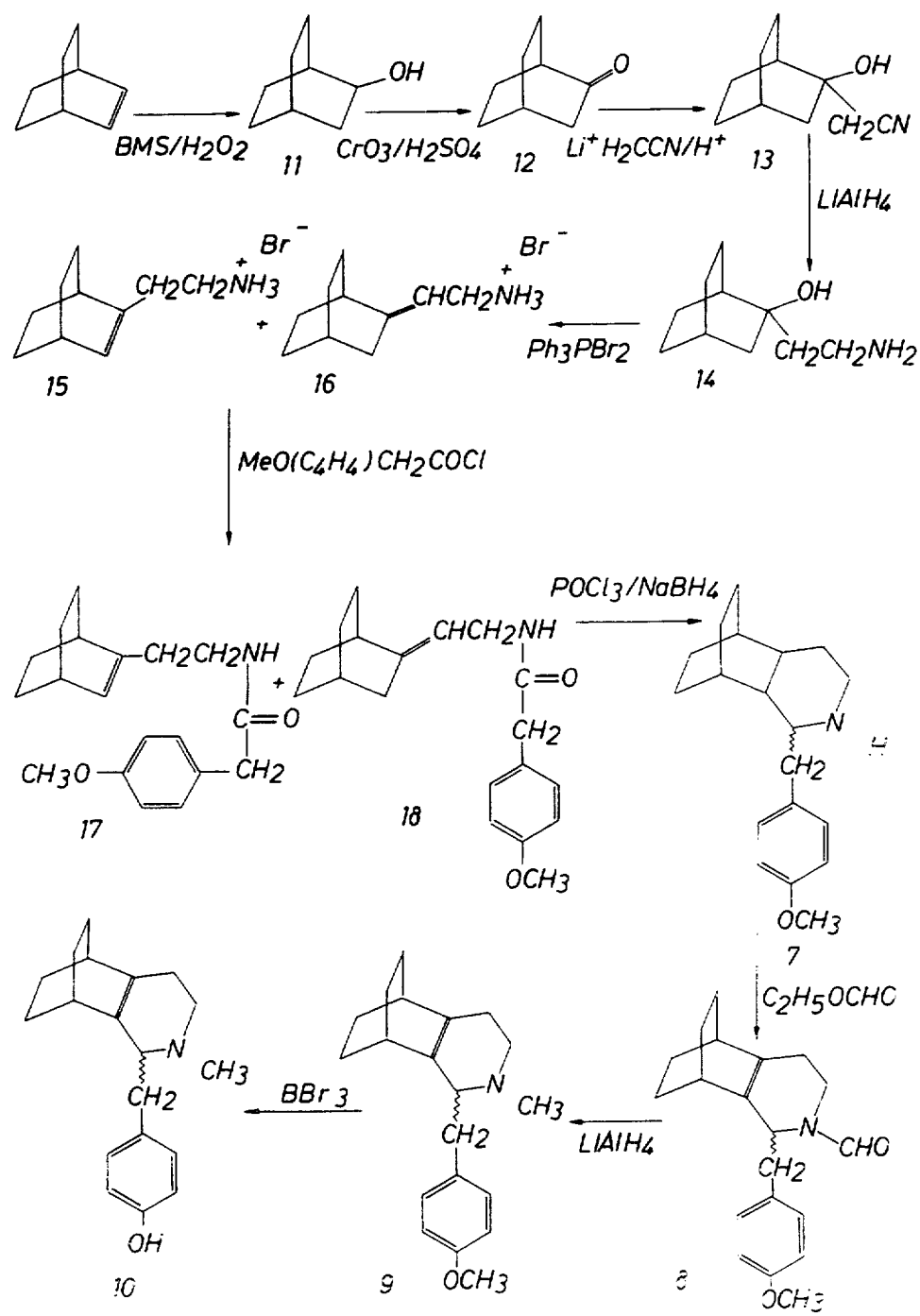
Figure 5:
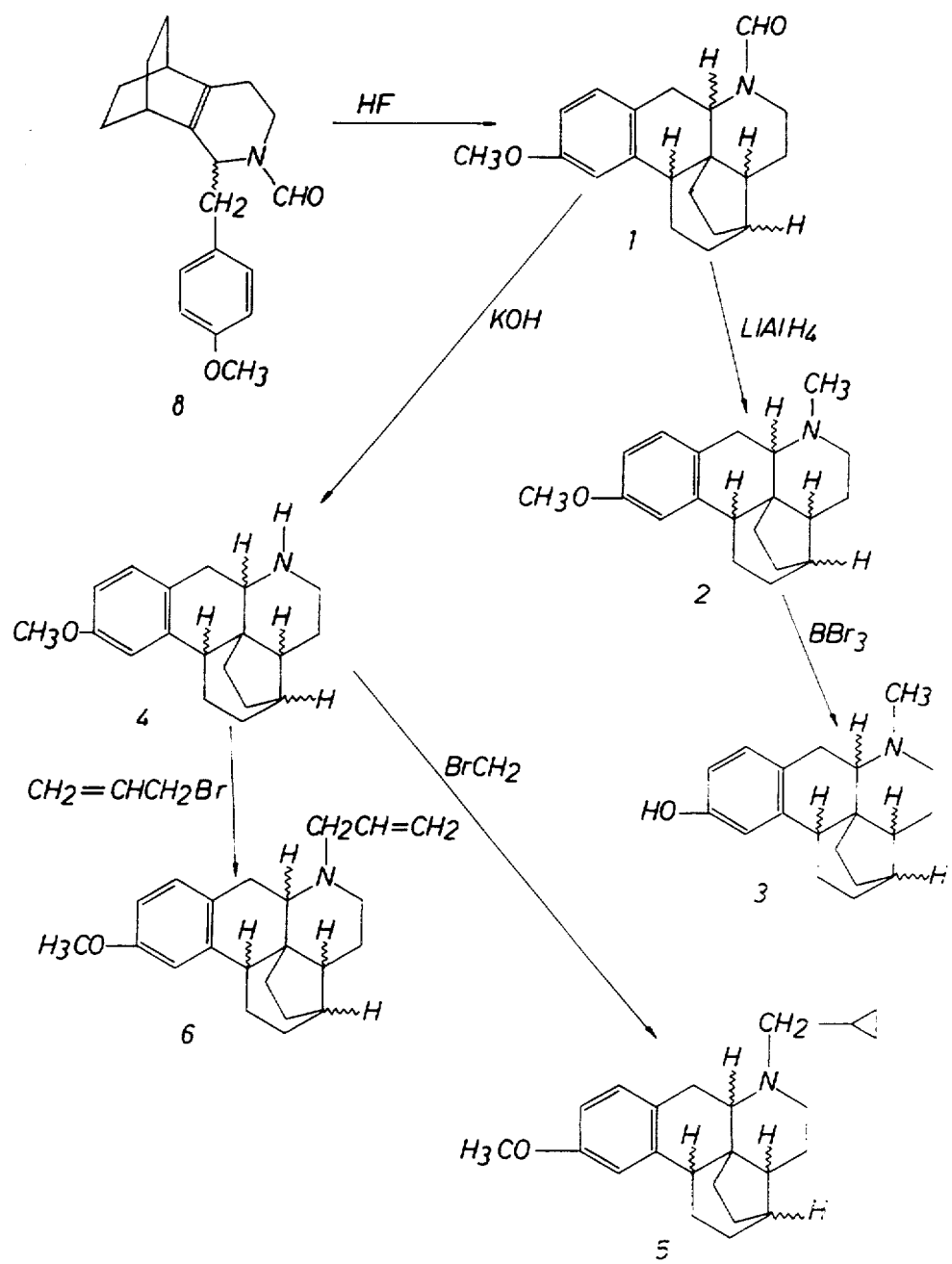
Figure 6:
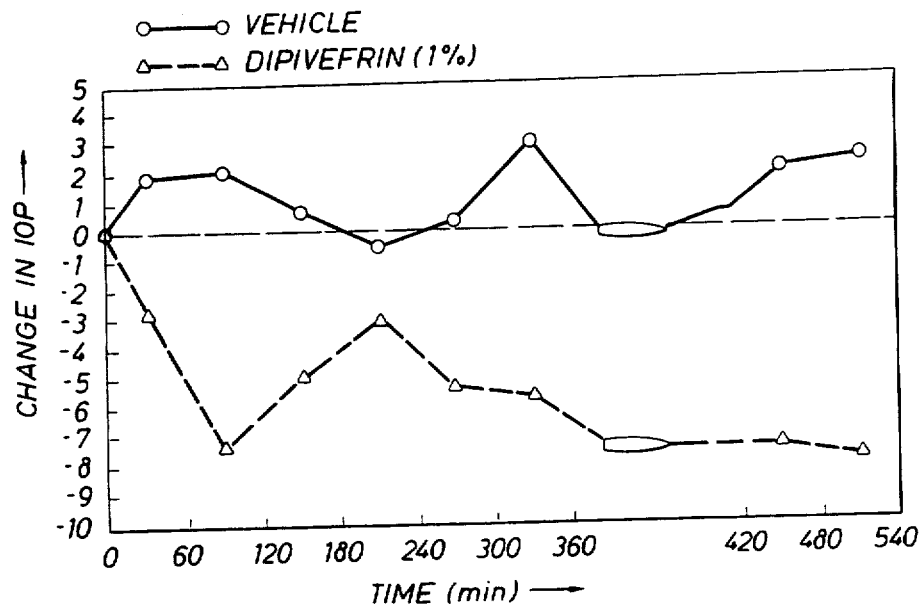
Figure 7:
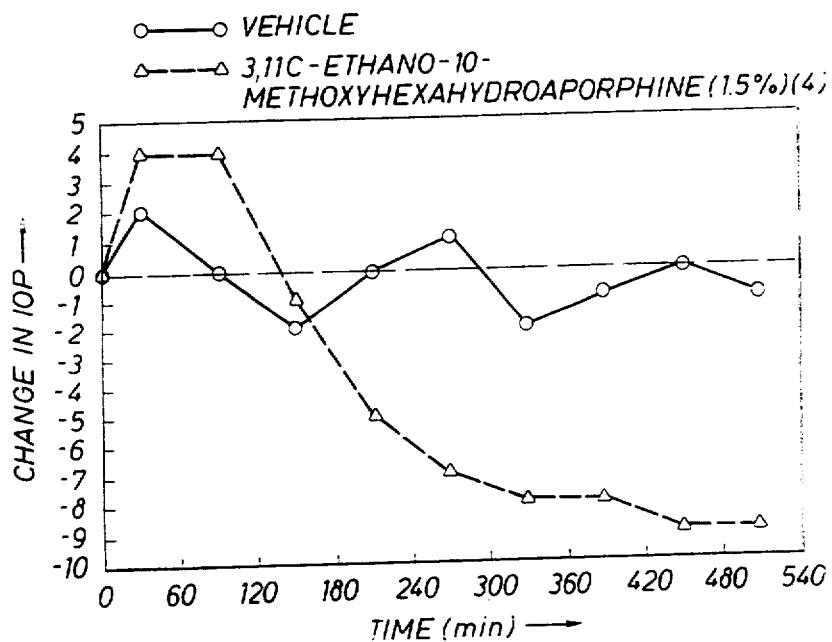
Figure 8:
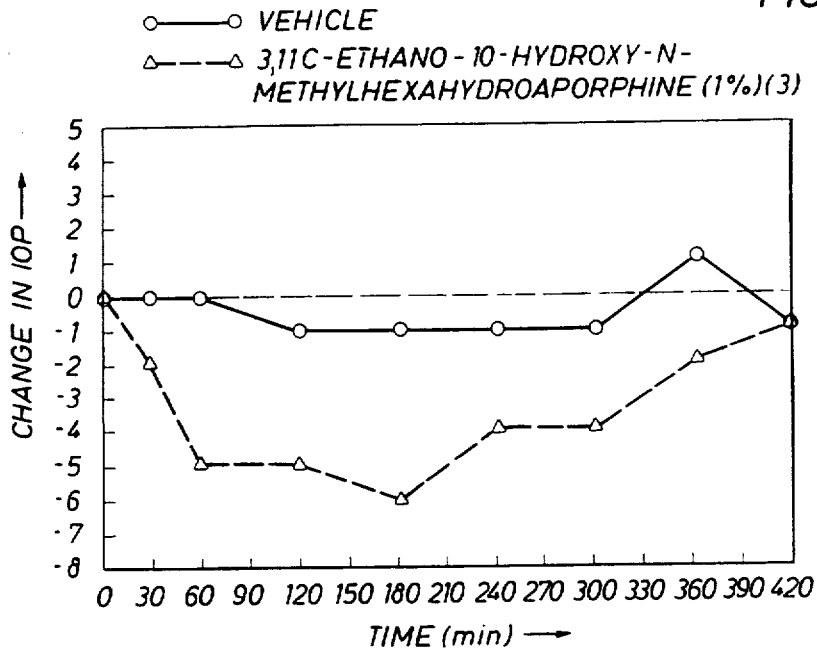
Figure 9:
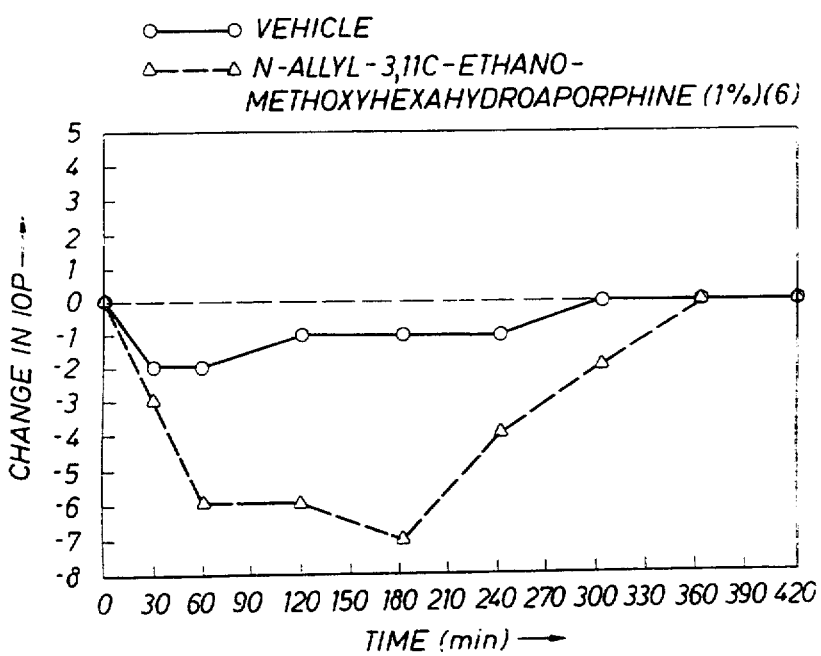
Figure 10:
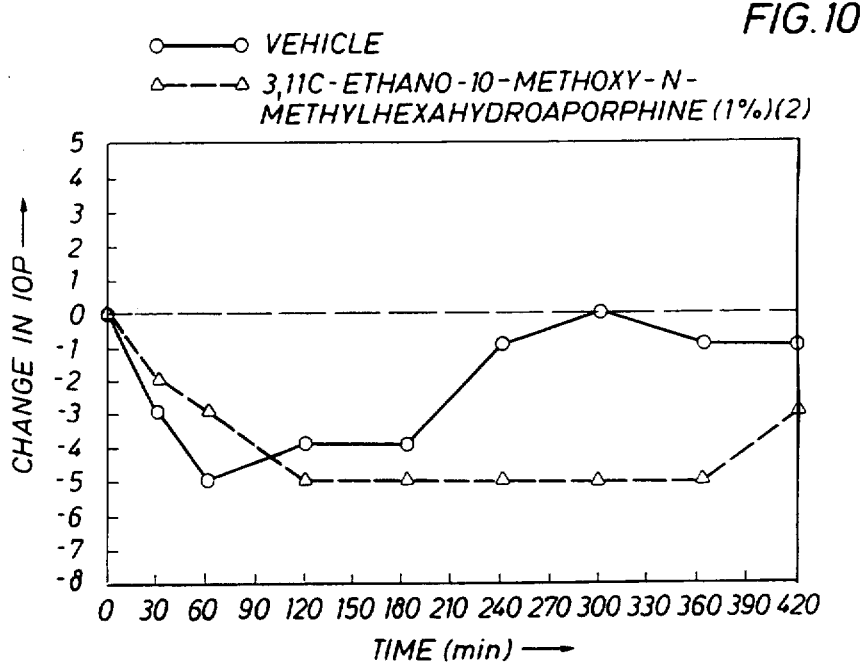
Figure 11:
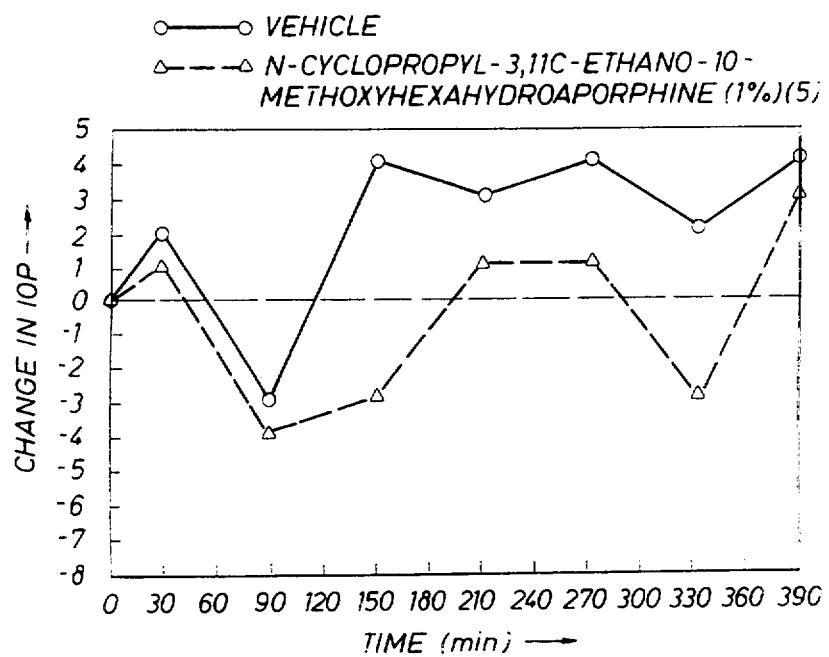

Compound 4 caused a dose-dependent (0.125% –1.5%) decrease in IOP in treated eyes of normotensive rabbits when compared to contralateral (vehicle treated) eyes (FIG. 7). The IOP lowering effect of bicyclic hexahydroaporphines was compared with that of dipivefrin (FIG. 6), a therapeutic agent currently employed in the treatment of glaucoma. At equivalent doses (1%), 3,4, and 6 elicited a 20% decrease in IOP which was similar to that obtained with dipivefrin (1%) (FIG. 6–9). Furthermore, we observed that 2 (1%) lowered IOP and induced a significant contralateral effect on vehicle treated eyes (FIG. 10). In contrast, 5 (1%) had a transient ocular hypotensive effect which lasted for about 30 mins. in normotensive animals (FIG. 11). These results strongly suggest that bicyclic hexahydroaporphines can lower IOP in normotensive rabbits.

C. Prophetic Examples

Figure 3:
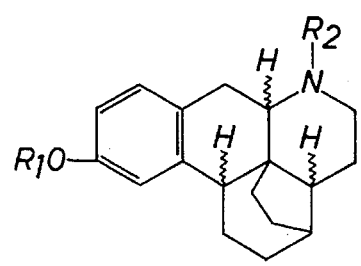
FIG. 3 is a diagrammatic illustration of the bicyclic hexahydroaporphines and 1-p-substituted benzyloctahydroisoquinolines included in the present invention.
Figure 3:
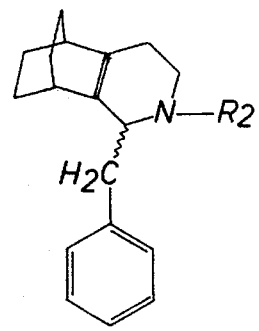

It is predicted that the bicyclic hexahydroaporphines and 1-p-substituted benzyloctahydroisoquinolines depicted in FIG. 3 are novel chemical entities that will be of therapeutic value in the treatment of glaucoma and other disease states characterized by ocular hypertension. The inherent lipophilicity of these molecules will permit rapid corneal penetration and subsequent trapping of drug in the eye upon topical administration. This efficacious delivery of active drug to the site of action should allow for the administration of lower doses than is required with more hydrophilic agents, which should, in turn, minimize potential side effects.

It is predicted that aqueous formulations of the compounds depicted in FIG. 3 which possess basic character will, in salt form, be able to be effectively applied directly to the eye, and provide a mechanism for drug delivery that is non-irritating and acceptable to patients. The aqueous solutions could also be administered by parenteral routes (e.g., IV or IM). It is also predicted that all molecules depicted in FIG. 3 could, in free base or formamide form, be efficiently formulated into an ointment base for direct application to the eye.

It is further predicted that the hydroxy group found on position 10 of the bicyclic hexahydroaporphine structure 3 and at the 13 position of the bicyclic octahydroisoquinoline 10 could be esterified with bulky, carbon rich acids (e.g., pivalic acid, t-butylacetic acid or cypionic acid), or alkylated to generate carbon rich ether analogs. These chemical modifications would provide lipophilic structures which would penetrate into the eye more efficaciously than the free phenol or methoxy ether derivatives. The lipophilic esters and ethers could certainly be active intact, and would also undergo slow metabolic conversion via hydrolysis (in the case of the esters) or O-dealkylation (in the case of the ethers) to release an active phenolic metabolite. This slow metabolic conversion of trapped parent drug to active metabolite should significantly increase the duration of intraocular pressure lowering activity compared to the parent structures.

As previously mentioned, it is predicted that, if the structures depicted in FIG. 3 are shown to bind to presynaptic catecholamine-based neurotransmitter receptors, they would find use in the treatment of hypertension through the central stimulation of prejunctional $\alpha_2$ receptors. The structures are lipophilic enough to cross the blood brain barrier and enter the central nervous system after parenteral administration. Those molecules which are capable of selectively stimulating postsynaptic $\beta_2$ receptors could find use in the treatment of respiratory disorders characterized by bronchoconstriction or bronchospasm. Finally, these compounds might find use in disease states which are characterized by abberations in dopamine neurotransmission.

We claim:

1. A pharmaceutical composition for controlling intraocular pressure, comprising:

(a) an intraocular pressure lowering amount of a bicyclic hexahydroaporphine, or an opthalmalogically acceptable derivative form thereof; and (b) an opthalmalogically acceptable vehicle thereof, wherein said vehicle is selected from the group consisting of a preservative, an antioxidant and a buffer.

2. The pharmaceutical composition of claim 1 wherein said ophthamologically acceptable antioxidant is at least one of sodium bisulfite and ascorbic acid.

3. The pharmaceutical composition of claim 1, wherein said pharmaceutical composition is between about 0.1 percent and about 5 percent bicyclic hexahydroaporphine.

4. The pharmaceutical composition of claim 1 wherein the functional group found on position 10 is at least one of a carbon rich ester and ether.

5. The pharmaceutical composition of claim 4 wherein said ester is active intact.

6. The pharmaceutical composition of claim 4 wherein said ester releases an active phenol during hydrolysis.

7. The pharmaceutical composition of claim 4 wherein said ether is active intact.

8. The pharmaceutical composition of claim 4 wherein said ether releases an active phenol during O-dealkylation.

* * * * *

UNITED STATES PATENT AND TRADEMARK OFFICE
CERTIFICATE OF CORRECTION

PATENT NO. : 5,512,577
DATED : April 30, 1996
INVENTOR(S) : Roche, et al

It is certified that error appears in the above-indentified patent and that said Letters Patent is hereby corrected as shown below:

In Figure 10, the legend should read --3,11C...--, not "3.11C".
   A comma should appear and not a period.
In Figure 11, the legend should read --3,11C...--, not "3.11C".
   A comma should appear and not a period.

Signed and Sealed this

Twenty-ninth Day of October 1996

BRUCE LEHMAN

*Attest:*

*Attesting Officer*     Commissioner of Patents and Trademarks

UNITED STATES PATENT AND TRADEMARK OFFICE
CERTIFICATE OF CORRECTION

PATENT NO. : 5,5,12,577
DATED : April 30, 1996
INVENTOR(S) : Roche, et al

Figure 1:
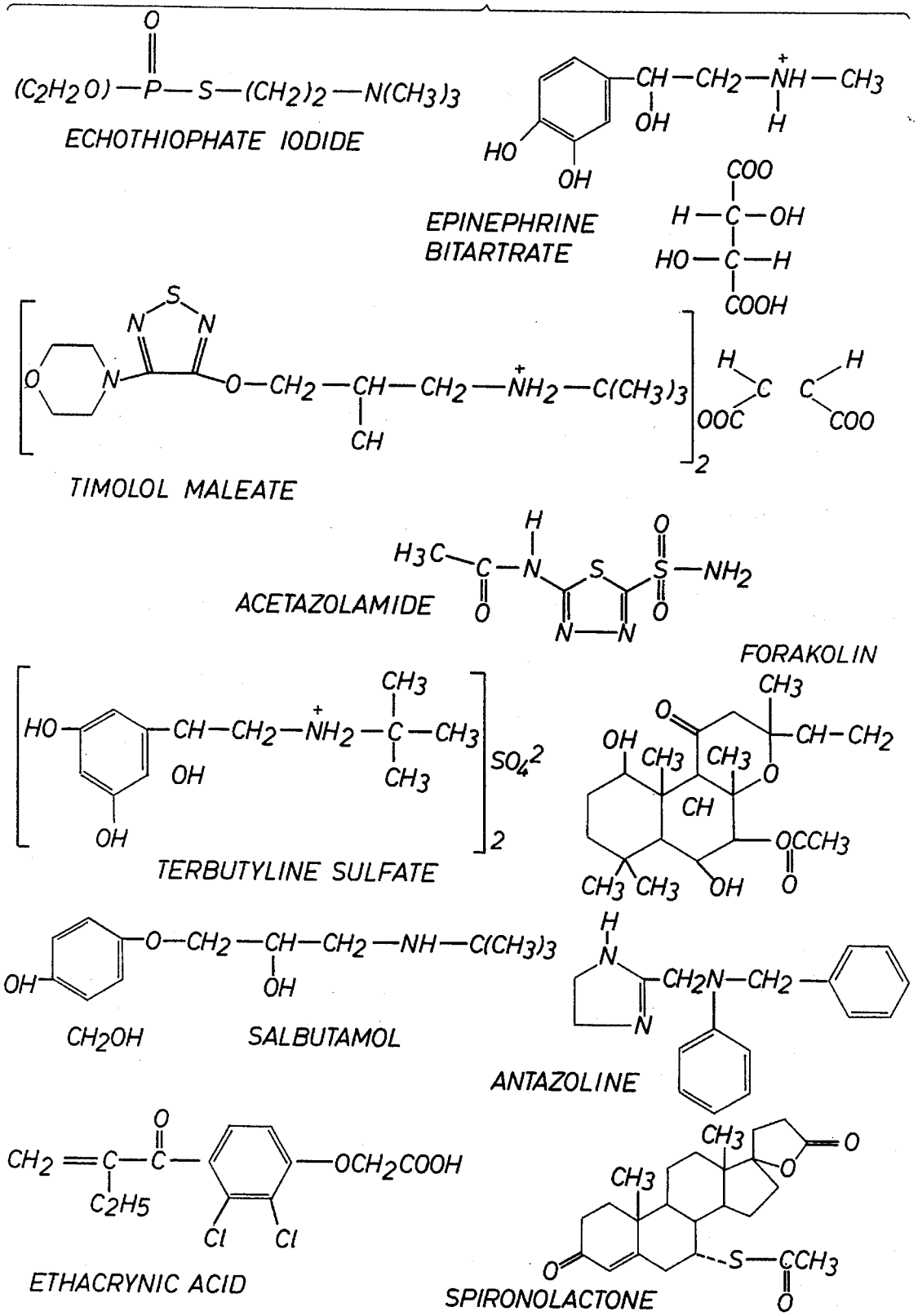
FIG. 1 is a diagrammatic illustration of selected therapeutic entities currently utilized, or under investigation, in the treatment of glaucoma and ocular hypertension.
Figure 2:
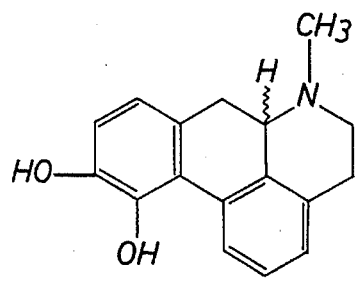
FIG. 2 is a diagrammatic illustration of the dopaminergic agonist apormorphine, an A-ring reduced apomorphine analog, and the opioid analgetic levorphanol.
Figure 2:
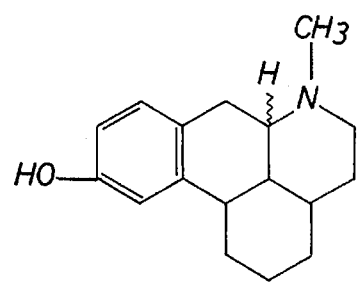
Figure 2:
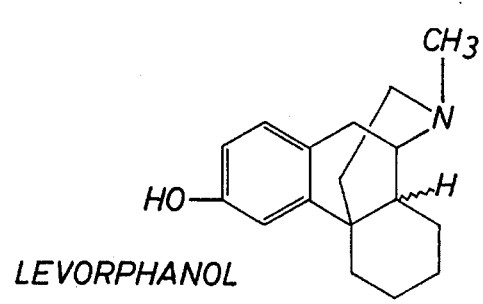

It is certified that error appears in the above-indentified patent and that said Letters Patent is hereby corrected as shown below:

In Figure 1, for Echothiophate Iodide, the first appearance of "H2" should read ---H5---.
In Figure 1, for Timolol Maleate the double bond was excluded.
In Figure 1, for Forakolin, a single bond was excluded.
In Figure 3, a single bond was excluded from the chemical structure pictured at the right.
In Figure 4, --- BBr3--- should be substituted in place of the "BBR3" pictured between Compounds 9 and 10.
Also in Figure 4, a single bond was excluded from Compound 8.
In Figure 5, a single bond was excluded from Compound 8.
Also in Figure 5, a single bond was excluded from Compound 2.
In Figure 7, the legend should read --3,11C...--, not "3.11C". A comma should appear and not a period.
In Figure 8, the legend should read --3,11C...--, not "3.11C". A comma should appear and not a period.
In Figure 9, the legend should read --3,11C...--, not "3.11C". A comma should appear and not a period.

APOMORPHINE

N-METHYL-10-HYDROXY-
HEXAHYDROAPORPHINE

LEVORPHANOL

| | $R_1$ | $R_2$ | | $R_1$ | $R_2$ |
|---|---|---|---|---|---|
| 1 | $CH_3$ | CHO | 7 | $CH_3$ | H |
| 2 | $CH_3$ | $CH_3$ | 8 | $CH_3$ | CHO |
| 3 | H | $CH_3$ | 9 | $CH_3$ | $CH_3$ |
| 4 | $CH_3$ | H | 10 | H | $CH_3$ |
| 5 | $CH_3$ | $CH_2$—◁ | | | |
| 6 | $CH_3$ | $CH_2CH=CH_2$ | | | |